United States Patent
Chavas et al.

(10) Patent No.: US 11,400,311 B2
(45) Date of Patent: Aug. 2, 2022

(54) DEVICE FOR ILLUMINATING AN OBJECT WITH A CONTROLLED LIGHT INTENSITY AND ASSOCIATED METHOD

(71) Applicants: GENSIGHT BIOLOGICS, Paris (FR); SORBONNE UNIVERSITÉ, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

(72) Inventors: Joël Chavas, Orsay (FR); Guillaume Chenegros, Trappes (FR); Benjamin R. Benosman, Pantin (FR)

(73) Assignees: GENSIGHT BIOLOGICS, Paris (FR); SORBONNE UNIVERSITÉ, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 135 days.

(21) Appl. No.: 16/310,490

(22) PCT Filed: Jun. 16, 2017

(86) PCT No.: PCT/EP2017/064827
§ 371 (c)(1),
(2) Date: Dec. 17, 2018

(87) PCT Pub. No.: WO2017/216371
PCT Pub. Date: Dec. 21, 2017

(65) Prior Publication Data
US 2019/0175934 A1    Jun. 13, 2019

(30) Foreign Application Priority Data
Jun. 17, 2016    (EP) .................................... 16305741

(51) Int. Cl.
*G02B 26/02* (2006.01)
*A61N 5/06* (2006.01)
(Continued)

(52) U.S. Cl.
CPC ........... *A61N 5/062* (2013.01); *A61N 5/0613* (2013.01); *A61N 5/0618* (2013.01);
(Continued)

(58) Field of Classification Search
None
See application file for complete search history.

(56) References Cited

U.S. PATENT DOCUMENTS

| 4,891,043 A | 1/1990 | Zeimer et al. |
| 5,521,392 A * | 5/1996 | Kennedy ................ A61N 5/062 250/492.1 |

(Continued)

FOREIGN PATENT DOCUMENTS

| CN | 1379647 A | 11/2002 |
| CN | 1434339 A | 8/2003 |

(Continued)

OTHER PUBLICATIONS

International Search Report and Written Opinion for International Application No. PCT/EP2017/064827, dated Dec. 21, 2017, 12 pages.

(Continued)

*Primary Examiner* — Erica S Lee
(74) *Attorney, Agent, or Firm* — Armstrong Teasdale LLP

(57) ABSTRACT

The invention concerns a device 10 for illuminating an object 12 with a controlled light intensity, the light intensity being controlled when the light intensity fulfills a plurality of conditions to be fulfilled, the plurality of conditions
(Continued)

comprising a condition relative to the intensity at a given time and a condition relative to the dose during a period of time.

11 Claims, 2 Drawing Sheets

(51) Int. Cl.
 *G02B 26/08* (2006.01)
 *G02F 1/01* (2006.01)
(52) U.S. Cl.
 CPC ........... *A61N 5/0622* (2013.01); *G02B 26/02* (2013.01); *G02B 26/0816* (2013.01); *G02F 1/0121* (2013.01); *A61N 2005/0626* (2013.01); *A61N 2005/0627* (2013.01); *A61N 2005/0628* (2013.01); *A61N 2005/0643* (2013.01); *A61N 2005/0652* (2013.01); *A61N 2005/0666* (2013.01)

(56) References Cited

U.S. PATENT DOCUMENTS

| | | | |
|---|---|---|---|
| 6,525,862 | B2 | 2/2003 | Fisher et al. |
| 6,781,691 | B2 | 8/2004 | Mackinnon et al. |
| 6,965,119 | B2 | 11/2005 | Sandström et al. |
| 7,146,983 | B1 | 12/2006 | Hohla et al. |
| 7,675,686 | B2 | 3/2010 | Lo et al. |
| 7,863,543 | B2 | 1/2011 | Bischoff et al. |
| 8,087,779 | B2 | 1/2012 | Levecq |
| 8,088,124 | B2 | 1/2012 | Loesel et al. |
| 8,235,973 | B2 | 8/2012 | Vogler et al. |
| 8,366,704 | B2 | 2/2013 | Lin et al. |
| 8,470,790 | B2 | 6/2013 | Pan et al. |
| 8,670,000 | B2 | 3/2014 | Braun et al. |
| 8,894,635 | B2 | 11/2014 | Behrakis |
| 8,906,360 | B2 | 12/2014 | Deisseroth et al. |
| 9,291,826 | B2 | 3/2016 | Domm |
| 9,435,752 | B2 | 9/2016 | Morton et al. |
| 9,528,819 | B2 | 12/2016 | Merschbach |
| 9,606,417 | B2 | 3/2017 | Hayakawa |
| 9,949,638 | B2 | 4/2018 | Creasey et al. |
| 10,031,326 | B2 | 7/2018 | Levecq et al. |
| 10,146,134 | B2 | 12/2018 | Godfried et al. |
| 2005/0288745 | A1 | 12/2005 | Andersen et al. |
| 2006/0139722 | A1 | 6/2006 | Kayser et al. |
| 2008/0009922 | A1 | 1/2008 | Bille |
| 2010/0097682 | A1 | 4/2010 | Angeley et al. |
| 2011/0051216 | A1 | 3/2011 | MacKinnon et al. |
| 2011/0222068 | A1 | 9/2011 | Heng |
| 2011/0295186 | A1 | 12/2011 | Klem |
| 2013/0030275 | A1 | 1/2013 | Seymour et al. |
| 2013/0129043 | A1* | 5/2013 | Morton ............... G01V 5/0008 378/62 |
| 2014/0121265 | A1 | 5/2014 | Pan et al. |
| 2014/0324135 | A1 | 10/2014 | Jones |
| 2015/0283399 | A1 | 10/2015 | Guglielmi et al. |
| 2017/0293229 | A1* | 10/2017 | Godfried ............... G03F 7/7085 |

FOREIGN PATENT DOCUMENTS

| | | |
|---|---|---|
| CN | 1582407 A | 2/2005 |
| CN | 1956752 A | 5/2007 |
| CN | 1985207 A | 6/2007 |
| CN | 101069106 A | 11/2007 |
| CN | 101287428 A | 10/2008 |
| CN | 101431975 A | 5/2009 |
| CN | 101484005 A | 7/2009 |
| CN | 101511523 A | 8/2009 |
| CN | 101564333 A | 10/2009 |
| CN | 101686873 A | 3/2010 |
| CN | 101715315 A | 5/2010 |
| CN | 102006833 A | 4/2011 |
| CN | 102271760 A | 12/2011 |
| CN | 103298394 A | 9/2013 |
| CN | 103930818 A | 7/2014 |
| CN | 103975250 A | 8/2014 |
| CN | 104287960 A | 1/2015 |
| CN | 104297947 A | 1/2015 |
| CN | 104546441 A | 4/2015 |
| CN | 104656358 A | 5/2015 |
| CN | 104737054 A | 6/2015 |
| CN | 204740398 U | 11/2015 |
| CN | 102822696 A | 4/2016 |
| CN | 105664379 A | 6/2016 |
| CN | 105683803 A | 7/2018 |
| EP | 0523417 A1 | 1/1993 |
| EP | 1470837 A2 | 10/2004 |
| EP | 1470837 A3 | 8/2005 |
| EP | 2088978 A1 | 8/2009 |
| EP | 2163936 B1 | 12/2012 |
| JP | 2004526188 A | 8/2004 |
| JP | 2017530398 A | 10/2017 |
| TW | 515707 B | 1/2003 |
| WO | 2002074339 A1 | 9/2002 |
| WO | 02063206 A3 | 10/2002 |
| WO | 2012076032 A1 | 6/2012 |
| WO | 2013071231 A1 | 5/2013 |
| WO | 2016045897 A1 | 3/2016 |

OTHER PUBLICATIONS

Barrett et al., "Optogenic approaches to retinal prosthesis." Visual Neuroscience (2014), 31, 354-354.
Ascrican et al., "Next-generation transgenic mice for optogenetic analysis of neural circuits." Frontiers in Neural Circuits (2013), 7. 24 pages.
Extract from Laser Institute of America, "American National Standard for Safe Use of Lasers ANSI Z136. Jan. 2014" (2014). 23 pages.
Navarro et al., "Monochromatic aberrations and point-spread functions of the human eye across the visual field." J. Opt. Soc. Am. A (1998), 15(9), 2522-2529.
Vann et al., "Optogenetics for neurodegenerative diseases." Int. J. Physiol Pathophysiol Pharmacol (2016), 8(1), 1-8.
Yan et al., "Maintaining ocular safety with light exposure, focusing on devices for optogenetic stimulation." Vision Research (2016), 121, 57-71.
Nagel et al. "Channelrhodopsin-2, a directly light-gated cation-selective membrane channel." Proceedings of the National Academy of Sciences (2003), 100(24), 13940-13945.
Lanyi, "Bacteriorhodopsin." Annu. Rev. Physiol. (2004), 66, 665-688.
Lanyi, "Halorhodopsin, a light-driven electrogenic chloride-transport system." Physiological Reviews (1990), 70(2), 319-330.
Klapoetke et al. "Independent optical excitation of distinct neural populations." Nature Methods (2014). 14 pages.
Extract from International Electrotechnical Commission. "CEI/IEC 62471: 2006, Photobiological Safety of Lamps and Lamp Systems." Geneva, Switzerland: International Electrotechnical Commission (2006). 13 pages.
Extract from International Organization for Standardization. "ISO 15004-2:2007, Ophthalmic instruments—Fundamental requirements and test methods—Part 2: Light hazard protection." International Organization for Standardization (2007). 11 pages.
Hamel. "Retinitis pigmentosa." Orphanet Journal of Rare Diseases (2006), 1(40). 12 pages.
Hadjinicolaou et al. "Prosthetic vision: devices, patient outcomes and retinal research." Clinical and Experimental Optometry (2015), 98, 395-410.
Degenaar et al. "Optobionic vision—a new genetically enhanced light on retinal prosthesis." Journal of Neural Engineering (2009), 6, 035007. 10 pages.
Grossman et al. "Multi-site optical excitation using ChR2 and micro-LED array." J. Neural. Eng. (2010), 7, 016004. 13 pages.
Busskamp et al. "Optogenetic therapy for retinitis pigmentosa." Gene Therapy (2012), 19, 169-175.

(56) References Cited

OTHER PUBLICATIONS

Boyden et al. "Millisecond-timescale, genetically targeted optical control of neural activity." Nature Neuroscience (2005), 8(9), 1263-1268.

* cited by examiner

DEVICE FOR ILLUMINATING AN OBJECT WITH A CONTROLLED LIGHT INTENSITY AND ASSOCIATED METHOD

CROSS-REFERENCE TO RELATED APPLICATIONS

The present application is the national stage entry of International Patent Application No. PCT/EP2017/064827, filed on Jun. 16, 2017, which claims the benefit of priority to European Patent Application No. 16305741.7, filed on Jun. 17, 2016, the contents of which are hereby incorporated by reference in their entirety.

TECHNICAL FIELD OF THE INVENTION

The invention relates to a device for illuminating an object with a controlled light intensity. The invention also relates to an associated method.

BACKGROUND OF THE INVENTION

Optogenetics is based in combining techniques from optic and genetics to control and monitor cell activities. It consists in (i) genetically modifying target cells in order to render them sensitive to light by the expression of exogenous photoreactive proteins in cellular membrane and (ii) providing illuminating device able to provide light to said photoreactive proteins.

It is an extremely powerful tool for selective neuronal activation/inhibition which can, for example, be used to restore neural functions in living animals, including humans (Boyden et al., 2005, *Nature Neuroscience* 8 (9): 1263-68), particularly in the eye (Busskamp et al., 2012, *Gene Therapy* 19 (2): 169-75).

It has been shown that selected wavelengths of light shall be close to the optimal wavelengths of the photoreactive proteins (Nagel et al. 2003, Proceedings of the National Academy of Sciences 100 (24): 13940-45, Klapoetke et al. 2014, *Nature Methods* 11 (3): 338-46) and that these proteins have a very low sensitivity to light (Asrican et al. 2013, *Front Neural Circuits*, 2013, 7:160; Busskamp et al. 2012, *Gene Therapy* 19 (2): 169-75). Therefore in order to obtain minimum level of protein activation by light, the intensity of light received by the target cell or protein shall be above a minimum value (Barrett et al., 2014, *Visual Neuroscience* 31 (4-5): 345-354).

However, while sufficient light must arrive at the photoreactive proteins to provide its activation, it is required to minimize tissue or cell heat and phototoxicity (Yan et al. 2016, *Vision Research* 121: 57-71). It is further desired to guarantee that the light dose for a given period of time will not cause any tissue or cell damages. Photobiological and ophthalmologic standards set thresholds for the intensity and for the dose are known in the art (see for example ISO 15004-2 2016; "ISO 62471:2006" 2016; § 8.3 of "ANSI Z136 Standards-LIA" 2014). Intensity is defined as the irradiance (in $mW/mm^2$ or $photons \cdot cm^{-2} \cdot s^{-1}$ and dose in a given period of time is defined as the integral of the intensity over the period of time ($mJ/mm^2$ or $photons \cdot cm^{-2}$).

Thus, it is desirable to provide illuminating device able to control intensity of light emitted and/or guaranteeing that the corresponding dose shall not exceed a maximum value.

Additionally there might be variability among patients in expressing exogenous photoreactive proteins, and threshold for photophobia is highly variable among patients (Hamel 2006, *Orphanet Journal of Rare Diseases* 1: 40) therefore it might be desirable to be able to adapt the intensity sent to the patient.

Similarly, the eye is itself an optical system with optical aberrations (Navarro, et al. 1998, *Journal of the Optical Society of America A* 15 (9): 2522), which include aberrations like myopia, hypermyopia and astigmatism. Optical aberrations are also present in emmetropic eyes and are taken into account in photobiological and ophthalmologic standards (ISO 15004-2, 2007; ISO 62471, 2006). These aberrations might reduce the light intensity received by photoactivable proteins, accordingly it might be desirable to provide illuminating device able to at least partially correct these drawbacks.

It is further desirable to provide illuminating device which are miniaturized so that it can be inserted in a device wearable by humans on a daily basis.

Currently available illuminating device to simulate the optogenetic proteins for in vitro experiments have been constructed (Degenaar et al. 2009, *Journal of Neural Engineering* 6 (3): 35007; Grossman et al. 2010, *Journal of Neural Engineering* 7 (1): 16004), but they are not miniaturized and are not yet suited for human use.

Head-Mounted displays are used for augmented reality, for virtual reality or for movie display.

However, the light intensity provided by these Head-Mounted Displays is not sufficient and is not configurable to stimulate photoreactive proteins and therefore are not adapted to optogenetics applications.

Therefore there is still strong need for an illuminating device which is adapted for illuminating an object with a controlled light intensity, especially when this object is living cell or tissue.

SUMMARY OF THE INVENTION

The invention aims at proposing a device for illuminating an object with a controlled light intensity which is easier to implement.

To this end, the invention concerns a device for illuminating an object with a controlled light intensity, the light intensity being controlled when the light intensity fulfills a plurality of conditions to be fulfilled, the plurality of conditions comprising a condition relative to the intensity at a given time and a condition relative to the dose during a period of time, the device comprising a light source adapted to produce a beam whose intensity does not fulfill at least one of the conditions to the fulfilled. The device comprises a photodiode adapted to measure the intensity of an incident beam and an optical system adapted to convey the light from an entrance to at least one exit, the light source, the photodiode and the optical system being arranged so that the device has two distinct configurations, an operating configuration in which a first portion of the light emitted by the light source is conveyed to the object, and a second portion of the light emitted by the light source is conveyed to the photodiode and a control configuration in which, in normal operating, no light produced by the light source is sent to object nor to the photodiode. The device also comprises a controller adapted to control the value of the first portion based on the intensity measured on the photodiode when the device is in the control configuration and based on the conditions to be fulfilled.

According to further aspects of the invention which are advantageous but not compulsory, the device might incorporate one or several of the following features, taken in any technically admissible combination:

one condition to be fulfilled is that the light intensity at any given time be inferior or equal to a maximum intensity.

one condition to be fulfilled is that the light intensity at any given time be superior or equal to a minimum intensity.

one condition to be fulfilled is that the dose during the period of time be inferior or equal to a maximum value.

the optical system comprises a plurality of reflectors, each reflector having three positions, a first position in which the reflector reflects the incident beam towards the object, a second position in which the reflector reflects the incident beam towards a photodiode and a third position in which the reflector reflects the incident beam neither to the object nor to the photodiode, the controller being adapted to command the position of each reflector, the device being in the operating configuration when the controller commands each reflector to be in the first position or in the second position and the device being in the control configuration when each reflector is commanded to be in the third position.

the controller is further adapted to deduce the number of reflectors to be moved in the first position based on the intensity measured on the photodiode when the device is in the control configuration and based on the conditions to be fulfilled and commanding the deduced number of mirrors to move in the first position.

the light source is a matrix of light sources, each light source having two states, an unfed state in which the light source emits no light and a fed state in which the source emits light, the controller being adapted to control the state of each light source.

a plane to be illuminated is defined for the object and wherein at least one of the light source and the optical system is such that the several independent spatial areas illuminated by different levels of intensity of light can be defined in the plane to be illuminated when the device is in the operating configuration.

the optical system comprises optical components ensuring that the point spread function be inferior to 30 μm, preferably inferior to 25 μm at the system output.

the optical system comprises a system adapted for correcting optical aberrations, the system adapted for correcting optical aberrations being adjustable.

the system adapted for correcting optical aberrations is a liquid lens.

the device is used in optogenetics, the object participating in restoring or improving the eyesight of a user of the device, the object comprising a plurality of cells expressing photoreactive proteins, the light intensity being controlled when the light intensity fulfills a plurality of conditions to be fulfilled in order to prevent any cellular and tissue damages.

The invention also relates to a method for illuminating an object with a controlled light intensity, the light intensity being controlled when the light intensity fulfills a plurality of conditions to be fulfilled, the plurality of conditions comprising a condition relative to the intensity at a given time and a condition relative to the dose during a period of time, the method comprising providing a device for illuminating an object with a controlled light intensity, the device comprising a light source adapted to produce a beam whose intensity does not fulfill at least one of the conditions to the fulfilled. The device comprises a photodiode adapted to measure the intensity of an incident beam and an optical system adapted to convey the light from an entrance to at least one exit, the light source, the photodiode and the optical system being arranged so that the device has two distinct configurations, an operating configuration in which a first portion of the light emitted by the light source is conveyed to the object, and a second portion of the light emitted by the light source is conveyed to the photodiode and a control configuration in which, in normal operating, no light produced by the light source is sent to object nor to the photodiode. The device also comprises a controller adapted to control the value of the first portion based on the intensity measured on the photodiode when the device is in the control configuration and based on the conditions to be fulfilled. The method also comprises the step of commanding the device to operate in the control configuration, measuring the intensity on the photodiode, determining an intensity illuminating the object due to an abnormal operating of the device in the control configuration based on the measured intensity, deducing the first portion of light to be emitted in the operating configuration based on the determined light intensity and on the conditions (C1, C2, C3) to be fulfilled, and commanding the device to be in the operating configuration with the value of the first portion being equal to the deduced first portion.

According to further aspects of the invention which are advantageous but not compulsory, the method might incorporate one or several of the following features, taken in any technically admissible combination:

the object is an object which restores or improves the eyesight of a user of the device.

the object comprises at least one cell expressing photoreactive proteins.

photoreactive protein is chosen in the group consisting of light-gated ion channel.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
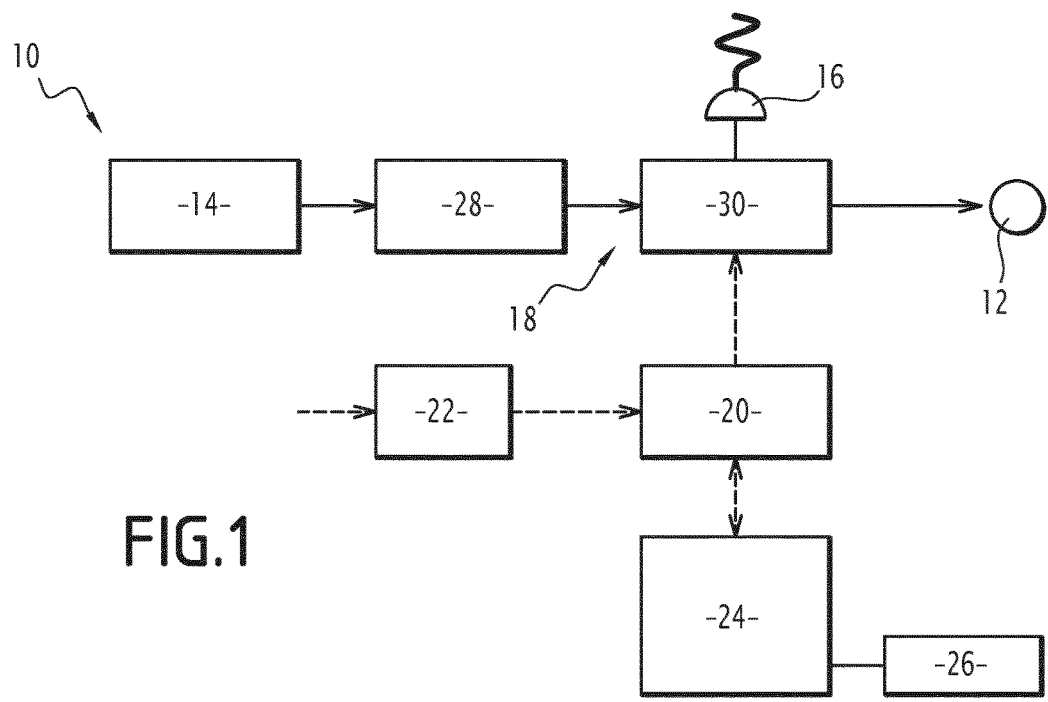
FIG. 1 shows schematically an example of device for illuminating an object, the device comprising reflector or beam splitter.

A device 10 for illuminating an object with a controlled light intensity and an object 12 are represented on FIG. 1.

The device 10 is adapted to illuminate the object 12 with a controlled light intensity.

The light intensity is considered as controlled when the light intensity fulfills a plurality of condition to be fulfilled.

The plurality of conditions comprises a condition relative to the intensity at a given time and a condition relative to the dose during a period of time For instance, one condition to be fulfilled is that the light intensity at any given time be inferior or equal to a maximum intensity. This condition is named first condition C1.

According to another example, one condition to be fulfilled is that the light intensity at any given time be superior or equal to a minimum intensity. This condition is named second condition C2.

According to still another example, one condition to be fulfilled is that the dose during the period of time be inferior or equal to a maximum value. For instance, the period of time is one hour, 12 hours, 24 hours or 48 hours. This condition is named third condition C3.

One condition to be fulfilled may also be relative to an intensity in a given interval of wavelengths.

The set of conditions can be chosen so as to respect a norm relative to the object, notably a medical one.

According to another example, one condition to be fulfilled is that the illuminated area does not extend beyond a given area.

According to another example, several independent spatial areas illuminated by different levels of intensity of light can be defined in a plane corresponding to the object 12. One condition to be fulfilled is a condition relative to the homogeneity of each level of intensity. As a specific example, a condition to be fulfilled is that the percentage of variation of level of intensity with respect to the mean level of intensity be inferior or equal to a maximum value.

According to another example, the object to illuminate is itself an optical system containing a diaphragm. Alternatively, the object to illuminate is the eye, whose diaphragm is the pupil. One condition to be fulfilled is that the percentage of the flux of the incident light passing through a given disk of the diaphragm be superior to a given value.

Another condition to be fulfilled is that the percentage of the flux of the incident light passing through any disk of a given diameter on the diaphragm plane be inferior to a given value.

According to another example, one condition to be fulfilled is that the percentage of the flux of the incident light passing through any disk of a given diameter over a given segment of the beam path be inferior to a given value. For example, this segment of the beam path over which this condition applies can be the anterior segment of the eye.

In the remainder of the specification, it is assumed that the plurality of conditions to be fulfilled by the device 10 is the three conditions C1, C2 and C3.

The device 10 of FIG. 1 comprises a light source 14, a photodiode 16, an optical system 18, a controller 20, a camera 22, a commanding unit 24 and a power source 26.

The light source 14 is adapted to produce a beam whose intensity does not fulfill at least one of the conditions to the fulfilled.

According to the specific example of FIG. 1, the light source 14 is adapted to produce a beam whose light intensity at any given time is superior or equal to a minimum intensity. This means that the light source 14 does not fulfill the first condition C1.

In the case of FIG. 1, the light source 14 is an electroluminescent diode.

The photodiode 16 is adapted to measure the intensity on an incident beam.

For instance, the photodiode 16 is made in the CMOS technology, the acronym CMOS referring to complementary metal oxide semi-conductor.

The optical system 18 is adapted to convey the light from an entrance to at least one exit.

In the case of FIG. 1, the optical system 18 is adapted to convey the light produced by the light source 14 to the object 12 according to one light path and to the photodiode 16 according to another light path.

The light source 14, the photodiode 16 and the optical system 18 are arranged so that the device 10 has two distinct configurations M1 and M2: an operating configuration M1 and a control configuration M2.

In the operating configuration M1, a first portion of the light emitted by the light source 14 is conveyed to the object 12 and a second portion of the light emitted by the light source 14 is conveyed to the photodiode 16.

In the control configuration M2, in normal operating, no light produced by the light source 14 is sent to object 12 nor to the photodiode 16. By normal operating, it is meant that each component of the device 10 is working according to its nominal operating. This means that each component of the device 10 operates in accordance with its commands In other words, in abnormal operating, at least one component of the device 10 does not operate in accordance with its command.

In the specific example of FIG. 1, the switch between the operating configuration M1 and the control configuration M2 is enabled by the optical system 18.

The optical system 18 comprises an optical conveyor 28 and a plurality of reflectors 30 schematically represented by boxes on FIG. 1, bearing in mind that the plurality of reflectors 30 belong to the optical conveyor 28.

The reflector 30 is usually a mirror.

The reflector 30 can also be a beam splitter.

According to a specific example, each reflector is a micromirror so that the plurality of reflectors 30 forms an array of micromirror.

Figure 2:
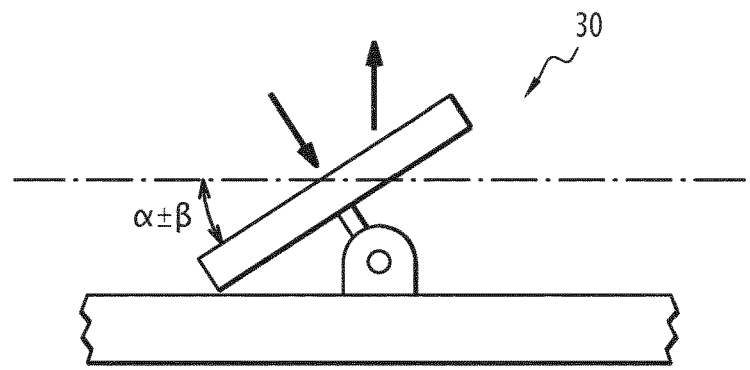
FIG. 2 shows schematically a reflector in a first position.
Figure 3:
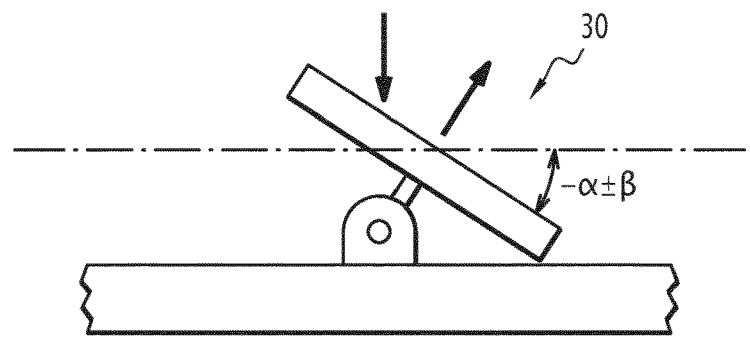
FIG. 3 shows schematically the reflector of FIG. 2 in a second position.
Figure 4:
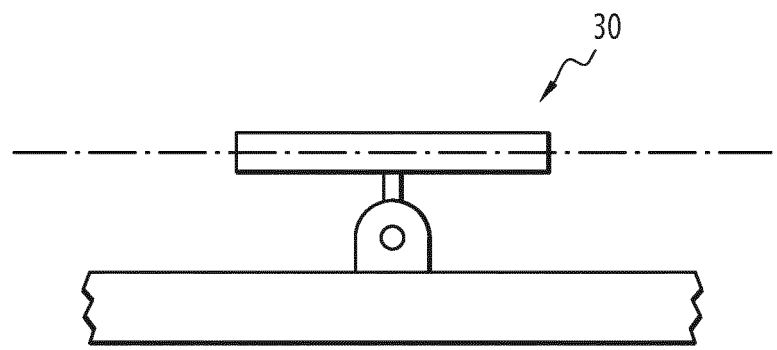
FIG. 4, shows schematically the reflector of FIG. 2 in a third position.

Each reflector 30 has three positions illustrated by FIGS. 2 to 4: a first position, a second position and a third position.

In the first position (see FIG. 2), the reflector 30 reflects the incident beam towards the object 12.

In the second position (see FIG. 3), the reflector 30 reflects the incident beam towards the photodiode 16.

In a third position (see FIG. 4), the reflector 30 reflects the incident beam neither to the object 12 nor to the photodiode 16.

In the illustrated example, the reflector 30 passes from one position to another by a rotation around a given axis.

Furthermore, the angle of rotation between the first position and the third position is equal to the angle of rotation between the third position and the second position.

The operating configuration M1 corresponds to a configuration wherein a first portion of the reflector 30 is in the first position while a second portion of the reflectors is in the second position.

The control configuration M2 corresponds to a configuration wherein each reflector 30 is in the third position.

Alternatively, the control configuration M2 corresponds to a configuration wherein each reflector 30 is in the first position.

In normal operating, no light produced by the light source 14 is sent to object 12 nor to the photodiode 16 in the control configuration M2.

By normal operating in this specific example, it is meant that each reflector 30 of the device 10 is in the position corresponding to the command sent to it. However, it occurs that reflectors 30 stay blocked in its position.

Thus, in abnormal operating, in the control configuration M2, a blocked reflector 30 may however send light to the object 12 or the photodiode 16.

This abnormal operating has to be taken into account to ensure that the light intensity fulfills the three conditions C1, C2 and C3. This is achieved by the controller 20.

The controller 20 is adapted to control the value of the first portion based on the intensity measured on the photodiode 16 when the device 10 is in the control configuration M2 and based on the three conditions C1, C2 and C3.

According to the example of FIG. 1, the controller 20 is adapted to command the position of each reflector 30.

The controller 20 is further adapted to take into account an eventual abnormal operating of the device 10 in the fulfilling of the conditions C1, C2, C3 to be fulfilled by the light intensity and deduce the number of reflectors 30 to be moved in the first position based on the intensity measured on the photodiode 16 when the device 10 is in the control configuration M2 and based on the conditions to be fulfilled C1, C2, C3 and to command the deduced number of reflectors 30 to move in the first position.

The controller 20 of FIG. 1 is also in interaction with the camera 22, the commanding unit 24 and the power source 26.

Power source can be for example one battery or alternatively an external 15V power source attached to the power grid.

The camera 22 is adapted to capture an exterior scene and send the exterior scene captured to the controller 20. The controller 20 is further adapted to convert the scene into a converted beam to be produced by the light source 20.

The controller 20 is commanded by the commanding unit 24 and the power source 26 in so far as the commanding unit 24 when the power source 26 is present is commanding the controller as an on/off switch.

The operating of the device 10 is now described in reference to a method for illuminating an object.

This method comprises a step providing the device 10.

The method also comprises a step of commanding the device 10 to operate in the control configuration M2.

In the illustrated example, the controller 20 commands each reflector 30 to be in the third position.

The method also comprises a step of measuring the intensity on the photodiode 16. In normal operating, the measured intensity on the photodiode 16 corresponds to noise. Noise is an intensity corresponding to number of mirrors switching from one position to one another.

This means that each reflector 30 is able to switch in the third position. No reflector 30 is blocked in its position.

In abnormal operating, a plurality of reflectors 30 is blocked in its position. As the blocking position is random, several reflectors 30 are blocked in the first position which means that the object 12 is illuminated by light produced by the light source 14.

Assuming a statistical sharing between the three positions, this also implies that several reflectors 30 are blocked in the second position and send light to the photodiode 16 to obtain a measured intensity. Any light intensity measured by the photodiode 16 when the device 10 is in the control configuration M2 results from abnormal operating of the device 10.

The method further comprises a step of determining an intensity illuminating the object 12 due to an abnormal operating of the device 10 in the control configuration M2 based on the measured intensity.

According to a specific embodiment, with the hypothesis of a statistical sharing of abnormal operating between the three positions, the step of determining is achieved by deducing the number of reflectors 30 in the second position, the number of reflectors 30 in the first position being assumed to be identical and by converting the number of reflectors 30 in the first position in light intensity illuminating the object 12. The converting operation depends from the optical system 18 considered.

The method also comprises a step of deducing the first portion of light to be emitted in the operating configuration M1 based on the determined light intensity and on the conditions to be fulfilled C1, C2, C3.

The method then comprises commanding the device 10 to be in the operating configuration M2 with the value of the first portion being equal to the deduced first portion.

This step is achieved by commanding the appropriate number of reflectors 30 to be in the first position.

The device 10 therefore enables to illuminate an object with a light intensity which fulfills a plurality of conditions and takes into account the abnormal operating of components of the device 10.

This results in the fact that the device 10 provides with an increased level of control of the light intensity.

In addition, the device is easy to implement in so far as the device 10 only requires a control configuration M2, a photodiode 16 and a controller 20.

Thus, others embodiments of the device 10 are to be considered.

Figure 5:
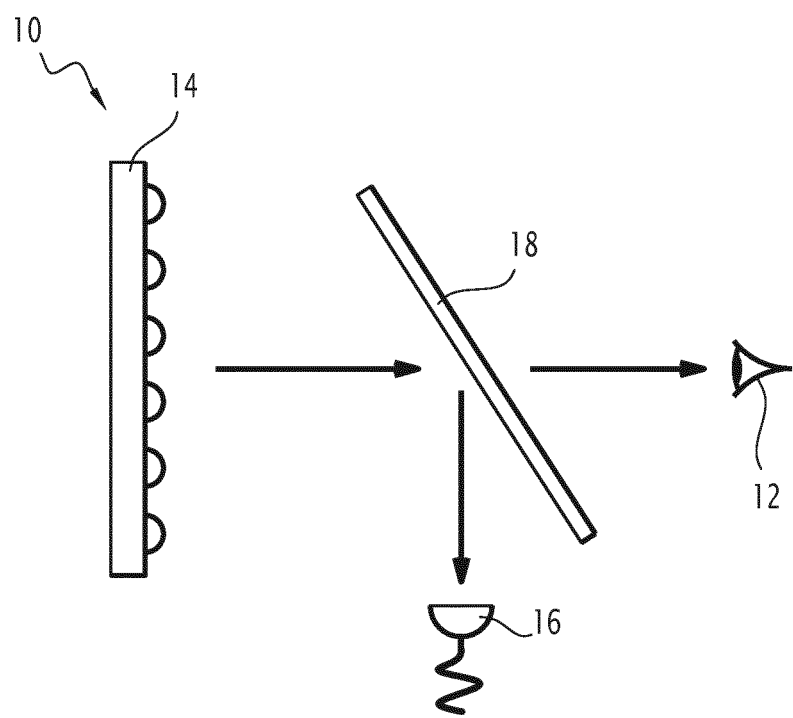
FIG. 5 shows another example of device for illuminating an object.

Another embodiment is described in reference to FIG. 5.

Each remark made in reference to the embodiment of FIG. 1 applies to the embodiment illustrated by FIG. 5. Only the differences are described.

In such case, the light source 14 is a matrix of electroluminescent diodes, each electroluminescent diode having two states, an unfed state in which the electroluminescent diode emits no light and a fed state in which the electroluminescent diode emits light.

The optical system 18 comprises a separator adapted to transmit a portion of light towards the object 12 and reflect a portion of light to the photodiode 16.

The controller 20 is adapted to control the state of each electroluminescent diode.

The operating configuration M1 corresponds to a configuration wherein several electroluminescent diodes are in the fed state. The first portion of light corresponds to the transmitted intensity through the optical system 18 while the second portion of light corresponds to the reflected intensity by the optical system 18.

The control configuration M2 corresponds to a configuration wherein electroluminescent diodes are in the unfed state. In normal operating, there is a full correspondence between the command of each electroluminescent diode and the state in which the electroluminescent diode is. In abnormal operating, this correspondence is not present.

The controller 20 enables to ensure that the absence of this correspondence be taken into account in the light sent to the object 12.

This embodiment of the device 10 also provides with an increased level of control of the light intensity.

Such device 10 may be useful for illuminating any kind of object 12.

According to specific example, the object to illuminate is itself an optical system with optical aberrations that can be measured in real-time or in offline conditions. These optical aberrations are characterized by its Point Spread Function (PSF). For example, if the object is the eye, these optical aberrations contain the defocus and astigmatism.

This implies constraints on the optical system 18.

One constraint to be fulfilled is that the standard deviation of the point spread function of the object plus the relevant part of the optical system 18 be below a maximum value.

Another example of constraint to be fulfilled is that the optical system 18 comprises optical components ensuring that the point spread function be inferior to 25 µm in each spatial area.

One example is an object 12 which is implemented in user of device 10 for treating and/or preventing neuropsychiatric and/or neurodegenerative diseases. Neurodegenerative diseases examples are retinopathies, Parkinson's disease, Huntington's disease, stroke, epilepsy, Alzheimer's disease (see for example Vann and Xiong, 2016, Int. J. Physiol. Pathophysiol. Pharmacol., 8, 1-8).

According to one preferred embodiment, said object 12 participates in restoring or improving the eyesight of a user of the device 10.

Indeed, for object 12 implemented in patient, the conditions, especially illuminating conditions, to be fulfilled are very strict in order to prevent any cellular and tissue damages.

For instance, the object 12 is retina, modified retina, retina cells, modified retina cells or a retina implant.

According to preferred embodiment, device of the invention is useful in optogenetics. Optogenetics is the combination of genetic and optical methods used to control specific events in targeted cells of living tissue. The hallmark of optogenetics is the expression of photoreactive proteins in target cells.

According to another preferred embodiment, the object 12 comprises a plurality of cells expressing photoreactive proteins.

As an example, the object 12 is the retina of an eye, said retina being modified for expressing plurality of photoreactive proteins.

According to a special embodiment, photoreactive protein is an opsin.

According to preferred embodiment, it is chosen in the group consisting of light-gated ion channel protein, and more specifically it is selected in the group consisting of Chrimson, ChrimsonR, (WO2013/71231), ChrimsonR-tdT, Catch, Channelrhodopsin (US20140121265, U.S. Pat. No. 8,906,360), and melanopsin and their derivatives. According to another special embodiment, photoreactive protein is chosen in the group consisting of light-gated ion pump such as bacteriorhodopsins (Lanyi, J K, 2004, *Annu Rev Physiol.* 66:665-88), halorhodopsins (Lanyi, J K, 1990, *Physiol Rev.* 70:319-30), and their derivatives.

Alternatively, the object 12 of the invention is electronic retinal prosthesis used in restoration of sight to patients blinded by retinal degeneration (see Hadjinicolaou et al. 2015, Clin Exp Optom., 98, 395-410.

Another example is an object 12 which is devoted to be eaten. For instance, the object 12 may be a vegetable.

The embodiments and alternative embodiments considered here-above can be combined to generate further embodiments of the invention.

What is claimed is:

1. A device for illuminating an object with a controlled light intensity, the controlled light intensity being controlled so that the controlled light intensity fulfills a plurality of conditions, the plurality of conditions comprising:
   one condition of the plurality of conditions is that the controlled light intensity at any given time be inferior or equal to a maximum intensity,
   one condition of the plurality of conditions is that the controlled light intensity at any given time be superior or equal to a minimum intensity, and
   one condition of the plurality of conditions is that the dose applied by the controlled light during a period of time be inferior or equal to a maximum value,
   the device comprising:
   a light source adapted to produce a beam of light having a first light intensity that does not fulfill at least one of the plurality of conditions based on at least one of:
     the first light intensity is superior to said maximum intensity,
     the first light intensity is inferior to said minimum intensity, and
     the dose applied by the first light during the period of time is superior to said maximum value,
   a photodiode adapted to measure a second light intensity of any light incident on the photodiode,
   an optical system comprising a plurality of reflectors, each reflector having a respective first, second, and third position, the light source, the photodiode and the optical system being arranged so that, for each reflector:
     in the first position, the reflector reflects any light produced by the light source that is incident thereon towards the object,
     in the second position, the reflector reflects any light produced by the light source that is incident thereon towards the photodiode, and
     in the third position, the reflector reflects any light produced by the light source that is incident thereon neither to the object nor to the photodiode, and
   a controller adapted to command the position of each reflector,
   wherein the device is in an operating configuration when the controller commands each reflector to be in the first position or the second position, thereby conveying a first portion of the light produced by the light source to the object and a second portion of the light produced by the light source to the photodiode,
   wherein the device is in a control configuration when the controller commands each reflector to be in the third position, and
   wherein the controller is further adapted to control the value of the first portion based on the light intensity measured on the photodiode when the device is in the control configuration and based on the plurality of conditions by: (i) detecting the device is experiencing abnormal operating in the control configuration by determining a third light intensity illuminating the object due to the abnormal operating of one or more of the reflectors in the control configuration, the one or more reflectors being blocked in a position different from the third position, (ii) deducing the first portion of light to be conveyed to the object when the device is in the operating configuration based on the determined third light intensity and on the plurality of conditions, and (iii) commanding the device to be in the operating configuration with the value of the first portion being equal to the deduced first portion.

2. The device according to claim 1, wherein the controller is further adapted to command the device to be in the operating configuration with the value of the first portion being equal to the deduced first portion by:
   deducing the number of reflectors to be moved into the first position based on the third light intensity measured on the photodiode when the device is experience abnormal operating in the control configuration and based on the plurality of conditions; and
   commanding the deduced number of reflectors to move into the first position.

3. The device according to claim 1, wherein the light source is a matrix of light sources, each light source having two states, an unfed state in which the light source emits no light and a fed state in which the light source emits light, the controller being adapted to control the state of each light source.

4. The device according to claim 1, wherein a plane to be illuminated is defined for the object and wherein at least one of the light source and the optical system is such that the several independent spatial areas illuminated by different levels of intensity of light can be defined in the plane to be illuminated when the device is in the operating configuration.

5. The device according to claim 4, wherein the optical system comprises optical components ensuring that the point spread function be inferior to 25 μm at the system output.

6. The device according to claim 5, wherein the optical system comprises a system adapted for correcting optical aberrations, the system adapted for correcting optical aberrations being adjustable.

7. The device according to claim 6, wherein the system adapted for correcting optical aberrations is a liquid lens.

8. A method for illuminating an object with a controlled light intensity, the controlled light intensity being controlled so that the light intensity fulfills a plurality of conditions, the plurality of conditions including:
   one condition of the plurality of conditions is that the controlled light intensity at any given time be inferior or equal to a maximum intensity,
   one condition of the plurality of conditions is that the controlled light intensity at any given time be superior or equal to a minimum intensity, and
   one condition of the plurality of conditions is that the dose applied by the controlled light during a period of time be inferior or equal to a maximum value,
the method comprising:
   providing a device for illuminating the object with the controlled light intensity, the device comprising:
      a light source adapted to produce a beam of light having a first light intensity that does not fulfill at least one of the plurality of conditions based on at least one of:
         the first light intensity is superior to said maximum intensity,
         the first light intensity is inferior to said minimum intensity, and
         the dose applied by the first light during the period of time is superior to said maximum value,
      a photodiode adapted to measure a second light intensity of any light incident on the photodiode,
      an optical system comprising a plurality of reflectors, each reflector having a respective first, second, and third position, the light source, the photodiode and the optical system being arranged so that, for each reflector:
         in the first position, the reflector reflects any light produced by the light source that is incident thereon towards the object,
         in the second position, the reflector reflects any light produced by the light source that is incident thereon towards the photodiode, and
         in the third position, the reflector reflects any light produced by the light source that is incident thereon neither to the object nor to the photodiode, and
      a controller adapted to command the position of each reflector,
      wherein the device is in an operating configuration when the controller commands each reflector to be in the first position or the second position, thereby conveying a first portion of the light produced by the light source to the object and a second portion of the light produced by the light source to the photodiode,
      wherein the device is in a control configuration when the controller commands each reflector to be in the third position, and
   commanding, by the controller, the device to operate in the control configuration,
   measuring the second light intensity on the photodiode,
   detecting the device is experiencing abnormal operating in the control configuration by determining a third light intensity illuminating the object due to the abnormal operating of one or more of the reflectors in the control configuration, the one or more reflectors being blocked in a position different from the third position,
   deducing, by the controller, the first portion of light to be conveyed to the object when the device is in the operating configuration based on the determined third light intensity and on the plurality of conditions, and
   commanding, by the controller, the device to be in the operating configuration with the value of the first portion being equal to the deduced first portion.

9. The method according to claim 8, wherein the object is an object which restores or improves the eyesight of a user of the device.

10. The method according to claim 8, wherein the object comprises at least one cell expressing photoreactive proteins.

11. The method according to claim 8, wherein photoreactive protein is chosen in the group consisting of light-gated ion channel.

* * * * *